United States Patent
Sommer et al.

(10) Patent No.: US 7,488,850 B2
(45) Date of Patent: Feb. 10, 2009

(54) PROCESS FOR REMOVING COMPOUNDS CONTAINING PHENOLIC HYDROXY GROUPS FROM AROMATIC AMINES

(75) Inventors: Knut Sommer, Krefeld (DE); Markus Dugal, Kempen (DE); Ido Schwarz, Düsseldorf (DE); Stefan Wershofen, Mönchengladbach (DE); Peter Lehner, Ratingen (DE); Stephan Schubert, Leverkusen (DE); Alexandra Große Böwing, Köln (DE)

(73) Assignee: Bayer MaterialScience LLC, Leverkusen (DE)

( * ) Notice: Subject to any disclaimer, the term of this patent is extended or adjusted under 35 U.S.C. 154(b) by 0 days.

(21) Appl. No.: 11/982,959

(22) Filed: Nov. 6, 2007

(65) Prior Publication Data

US 2008/0139850 A1    Jun. 12, 2008

(30) Foreign Application Priority Data

Nov. 10, 2006    (DE) .................... 10 2006 052 989

(51) Int. Cl.
*C07C 209/84*    (2006.01)
(52) U.S. Cl. .................... 564/437; 564/420; 564/421; 564/422; 564/423; 564/438; 564/439
(58) Field of Classification Search .................... None
See application file for complete search history.

(56) References Cited

U.S. PATENT DOCUMENTS

| 3,136,818 A | 6/1964 | Sperber et al. ............... 260/580 |
| 3,871,445 A | 3/1975 | Wanka et al. ............... 165/107 |
| 5,808,157 A | 9/1998 | Langer et al. ............... 564/422 |
| 5,877,350 A | 3/1999 | Langer et al. ............... 564/423 |
| 2005/0080294 A1 * | 4/2005 | Renner et al. ............... 564/437 |

FOREIGN PATENT DOCUMENTS

| DE | 34 14 714 C2 | 6/1986 |
| JP | 49-35341 | 4/1974 |
| JP | 08-295654 | 11/1996 |
| SU | 592436 | 2/1978 |

OTHER PUBLICATIONS

Wiberg, N., Hollemann-Wiberg—Lehrbuch der Anorganischen Chemie, 101st edition, (month unavailable) 1995, p. 939, note 166, Gerustsilicate ("Tectorsilicate").

* cited by examiner

*Primary Examiner*—Brian J Davis
(74) *Attorney, Agent, or Firm*—Lyndanne M. Whalen

(57) ABSTRACT

Compounds containing phenolic hydroxy groups are removed from a gas stream which contains at least one aromatic amine generated during the gas-phase hydrogenation reaction of the corresponding nitroaromatic compounds with hydrogen, by adsorption on a basic solid.

9 Claims, No Drawings

PROCESS FOR REMOVING COMPOUNDS CONTAINING PHENOLIC HYDROXY GROUPS FROM AROMATIC AMINES

BACKGROUND OF THE INVENTION

The present invention relates to a process for removing compounds containing phenolic hydroxy groups from a gas stream containing at least one aromatic amine generated during the gas-phase hydrogenation of the corresponding nitroaromatic compounds with hydrogen, by adsorption on a basic solid. As used herein, "compounds containing phenolic hydroxy groups" are compounds that carry at least one hydroxy group on an aromatic ring. In the case of the preparation of aniline and the purification of the aniline, the impurity carrying phenolic hydroxy groups is substantially phenol itself or alternatively derivatives that, in addition to the OH function, also carry other functional groups, such as, for example, the various aminophenols.

Aromatic amines are important intermediates which must be available inexpensively and in large amounts. It is therefore necessary, for example for the hydrogenation of nitrobenzene to aniline, to build plants having very large capacities. Aniline is an important intermediate, for example for the preparation of methylenediphenyl diisocyanate (MDI), and is generally produced on an industrial scale by catalytic hydrogenation of nitrobenzene with hydrogen (See, e.g., DE-OS 2201528; DE-OS 3414714; U.S. Pat. No. 3,136,818; EP 0 696 573 B1; and EP 0 696 574 B1). In this reaction, secondary components containing phenolic hydroxy groups such as phenol itself or aminophenols, are formed in addition to the desired product aniline. These secondary components must be removed in subsequent processes by distillation before the aniline is used further. The separation of phenol and aniline represents a major challenge for the distillation technique because their boiling points are very close together. The difficulty of separating phenol and aniline is reflected in the use of long distillation columns with a large number of plates and high reflux ratios, with a correspondingly high outlay in terms of investment and energy.

More recent approaches to separating phenol and aniline describe the use of soluble alkalis for the extraction or the addition of an alkali during the distillation. For example, JP-A-49-035341 describes an alternative process in which the crude aniline is brought into contact in a fixed bed with a solid alkali material (e.g., solid sodium hydroxide) and only then passed into the distillation, or in which the distillation is carried out in the presence of the solid alkali in a concentration of from 0.1 to 3 wt. %, based on the amount of aniline to be distilled. The separation of color-critical components such as aminophenols is thereby simplified.

However, disadvantages of this process are that high molar excesses of the solid alkali are used, based on the acidic secondary components that are to be removed, and that precise dosing of the alkaline compounds is not possible. This can, in the case of overdosing, lead to corrosion problems, precipitations and highly viscous semi-solid phases in the distillation column. Underdosing may lead to incomplete removal of the critical components.

As an alternative method for removing compounds containing phenolic hydroxy groups from aniline by distillation, JP-A-08-295654 describes extraction with dilute aqueous sodium hydroxide solution (or potassium hydroxide solution). In this disclosed method, most of the phenol is transferred, in the form of sodium phenolate, into the aqueous phase, which is separated off as the upper phase by subsequent phase separation. A molar NaOH:phenol ratio in the range from 3:1 to 100:1 is required to achieve an effective reduction in the phenol content. Disadvantages of this process are the high NaOH consumption (molar excesses), the formation of alkali-phenolate-containing waste water, which results in additional disposal costs, and an additional investment for the extraction.

SUMMARY OF THE INVENTION

The object of the present invention was, therefore, to provide a simple and economical process for purifying aromatic amines prepared by catalytic hydrogenation of the corresponding nitro compounds without the need for complex distillation while reducing the volume of the waste-water streams.

DETAILED DESCRIPTION OF THE INVENTION

The present invention relates to a process for removing compounds containing phenolic hydroxy groups from a gas stream which contains at least one aromatic amine which is generated during the gas-phase hydrogenation of the corresponding nitroaromatic compounds with hydrogen. In this process, the compounds containing phenolic hydroxy groups are adsorbed on a basic solid.

The basic properties of the basic solid preferably enable that basic solid to adsorb compounds containing phenolic hydroxy groups due to the acidic properties of the compounds containing phenolic hydroxy groups. The basic solid employed in the process of the present invention, preferably when it is fully loaded, can then be regenerated. The regeneration can be carried out, for example, by treatment with oxygen or oxygen-containing gas mixtures at elevated temperature. The adsorption can be carried out in a fixed bed of sufficiently large capacity or by operating a plurality of fixed beds in turn, it being possible for the fixed beds that are not in use to be regenerated.

In the process of the present invention, compounds containing phenolic hydroxy groups are adsorbed on the basic solid. The gas stream passed over the basic solid preferably has an inlet temperature of from 150 to 500° C. and an absolute pressure of from 1 to 50 bar. When the basic solid is fully loaded, it can be regenerated by treatment with oxygen or oxygen-containing gas mixtures at elevated temperature. The adsorption is preferably carried out either in one fixed bed of sufficiently large capacity or by operating a plurality of fixed beds in turn, the fixed beds that are not in use then preferably being regenerated.

The gas stream containing at least one aromatic amine that is used can come from any technically conventional process for the gas-phase hydrogenation of nitroaromatic compounds. The hydrogenation is preferably carried out on stationary, heterogeneous supported catalysts, such as Pd on aluminum oxide or carbon supports, in fixed-bed reactors at an absolute pressure of from 1 to 50 bar and a temperature in the range of from 150 to 600° C. under adiabatic conditions in gas loop mode (i.e., with recirculation of hydrogen not reacted during the hydrogenation). The process is described, for example, in EP 0 696 573 B1 and EP 0 696 574 B1.

The preferred aromatic amine is aniline.

There can be used as the basic solids any Brønsted-basic inorganic compounds of any of the elements in Groups 1, 2, 12, 13 and 14 of the Periodic Table of the Elements (nomenclature according to IUPAC recommendation of 1986), in particular, the oxides and hydroxides of the mentioned elements, and combinations of such inorganic compounds.

MgO, hydrotalcite and basic $Al_2O_3$ are preferred. Basic $Al_2O_3$ is particularly preferred. The basic inorganic compounds can be present either as such or on a suitable support. Suitable supports are any materials conventional in heterogeneous hydrogenation catalysis. Examples of suitable supports are disclosed in EP 0 696 573 B1 and EP 0 696 574 B1. α-Aluminum oxides and graphites or graphite-containing carbon supports are particularly suitable.

Basic zeolites can also be used as the basic solid. Such zeolites are described, for example in:

Rep, M.; Palomares, A. E.; Eder-Mirth, G.; van Ommen, J. G.; Rösch, N.; Lercher, J. A., "Interaction of Methanol with Alkali Metal Exchanged Molecular Sieves. 1. IR Spectroscopic Study", *Journal of Physical Chemistry B* (2000), 104 (35), 8624-8630;

Tsyganenko, A. A.; Kondratieva, E. V.; Yanko, V. S.; Storozhev, P. Yu., "FTIR study of CO adsorption on basic zeolites", *Journal of Materials Chemistry* (2006), 16 (24), 2358-2363; and Plant, David F.; Simperler, Alexandra; Bell, Robert G., "Adsorption of methanol on zeolites X and Y. An atomistic and quantum chemical study", *Journal of Physical Chemistry B* (2006), 110 (12), 6170-6178.

Preferred zeolites include: $Cs_mX$, $Cs_mY$, $Cs_mNa_nX$, $Cs_mNa_nY$, $Rb_mX$ and $Rb_mY$, in which the stoichiometry coefficients "m" and "n" can have any desired value (including zero), with the boundary condition that the sum of the two must compensate for the negative charge of X or Y (electroneutrality condition). Such zeolites are generally water-containing; for the sake of simplicity, the water was not included in the above formulae. The definitions of the terms "X" and "Y" are given in Wiberg, N., "Hollemann-Wiberg—Lehrbuch der Anorganischen Chemie", 101st edition, Walter de Gruyter, Berlin, N.Y. 1995, p. 939, note 166, to which reference is hereby made.

The basic solids used preferably have a very high adsorption selectivity with respect to compounds containing phenolic hydroxy groups. The adsorption selectivity A is the expression $$A = \frac{B}{B + x_B/x_C \cdot C} \cdot 100\%$$

in which the symbols used have the following meanings:
B=moles of compounds containing phenolic hydroxyl groups adsorbed per kg of basic solid,
C=moles of aromatic amine adsorbed per kg of basic solid,
$x_B/x_C$=weighting factor, which takes into account the high amine excess,
$x_B$=molar ratio (mol fraction) of the content of compounds containing phenolic hydroxy groups to the sum of the content of compounds containing phenolic hydroxy groups and the amine content in the mixture used,
$x_C$=molar ratio (mol fraction) of the amine content to the sum of the content of compounds having phenolic hydroxy groups and the amine content in the mixture used.

The adsorption selectivity is determined by experiment. More specifically, a gaseous stream of 49.12 g/h of aniline (doped with 500 ppm of phenol), 20.1 g/h of water and 24.5 l/h of hydrogen are passed, at ambient pressure, through an adsorber tube having a length of 60 cm and a diameter of 2.5 cm which is heated externally to 240° C. and filled with glass beads and a packing of 14 g of the adsorbent. The gas stream leaving the adsorber is condensed at 3° C. in a collecting vessel, and the phenol content is determined by gas chromatography. The adsorbent is extracted separately for 4 hours with isopropanol in a Soxhlet extractor, and the aniline and phenol contents of the distillate are determined by gas chromatography.

Preferred basic solids have an adsorption selectivity A of >90%, more preferably >98%, most preferably >99.5%. It is preferred to use MgO. Basic aluminum oxides are the most preferred adsorption agents.

The gas stream passed over the basic solid, which gas stream contains the amine to be purified, has an inlet temperature of preferably from 150 to 500° C., more preferably from 200 to 300° C., most preferably from 220 to 280° C., and an absolute pressure of preferably from 1 to 50 bar, more preferably from 2 to 20 bar, most preferably from 2 to 10 bar.

In a particularly advantageous embodiment of the process of the present invention, the procedure is carried out under conditions that are based on requirements of the hydrogenation reaction, for example, at the temperature and pressure of the product gas mixture after leaving the last heat exchanger in a production line.

In a particularly economical form of the process of the present invention, the basic solid is the same as the support or is applied to the support which is also used as the support for the hydrogenation-active metals in the hydrogenation of the nitro compound. In such a case, a separate downstream fixed bed with an additional basic solid is superfluous.

It is possible either to use a support which possesses the desired basic properties of the adsorption material from the outset or a support which has been modified by application of basic inorganic compounds before or, preferably, after it has been loaded with the hydrogenation-active metal(s).

When the adsorption capacity of the basic solid(s) is exhausted, it/they can be regenerated by treatment with oxygen or oxygen-containing gas mixtures at an elevated temperature of preferably from 250 to 500° C. in order to recover the original adsorption capacity. When a fixed bed of sufficiently large capacity is used, the regeneration is preferably carried out together with the regeneration of the hydrogenation catalyst. When a plurality of fixed beds are operated in turn, in each case one fixed bed is used for the adsorption and the others are regenerated in the meantime. If the basic solid is identical with the support of the hydrogenation-active metals or is applied thereto, its adsorption capacity is restored during the regeneration of the hydrogenation catalyst.

In order to facilitate regeneration, the basic solids can be provided with suitable oxidation catalysts. Suitable oxidation catalysts include the metals or metal oxides of Groups 5 to 7 or 10 and 11 of the Periodic Table of the Elements (nomenclature according to IUPAC recommendation of 1986), with preference being given to oxides of vanadium. These oxidation catalysts are generally present in amounts of from 0.1 to 10 wt. %, based on the total weight of the basic solid (including oxidation catalyst).

Further working-up steps, such as, for example, distillation or washing steps, can be provided downstream in order to achieve even higher degrees of purity of the aromatic amine, but such steps are not absolutely necessary. The downstream washing and/or distillation steps can be in the form of any variants known to those skilled in the art and can be operated under very different conditions. For example, a distillation can take place in one or more bubble plate or packed columns or in partition columns. Low-boilers and high-boilers can be separated in different columns or alternatively together in one column with removal of the aniline as a side stream.

The purified aromatic amines obtainable in the process according to the invention contain in total, based on the weight of the amine, preferably less than 0.01 wt. %, more preferably less than 0.005 wt. %, most preferably less than 0.002 wt. %, phenolic compounds. "Phenolic compounds" is to be understood as meaning the sum of all compounds containing phenolic hydroxy groups and their metal salts.

The aromatic amines obtained by the process of the present invention are particularly suitable for further large-scale use because of their high purity. For example, aniline purified by the process of the present invention can be reacted with formaldehyde, in the presence of an acid catalyst, in accordance with methods known in the art, to give di- and poly-amines of the diphenylmethane series. The di- and poly-amines obtained can then be reacted in accordance with processes known in the art, for example with phosgene, to give the corresponding di- and poly-isocyanates of the diphenylmethane series.

EXAMPLES

Examples for carrying out the process according to the invention are given below. Analysis of the phenol contents in the Examples which follow is carried out by means of gas chromatography.

Example 1

A gaseous stream of 49.12 g/h of aniline (doped with 500 ppm of phenol), 20.1 g/h of water and 24.5 l/h of hydrogen was passed, at ambient pressure, through an adsorber tube having a length of 60 cm and a diameter of 2.5 cm which was heated externally to 240° C. and filled with glass beads and a packing of 14 g of the adsorbent. The gas stream leaving the adsorber was condensed at 3° C. in a collecting vessel, and the phenol content was determined by gas chromatography. The adsorption time was 6 hours. Table 1 contains the adsorption capacities and selectivities that were found.

TABLE 1

| Adsorbent | Adsorbed amount in $g_{phenol}/kg_{adsorbent}$ | Adsorption selectivity A in % |
|---|---|---|
| $Al_2O_3$ (Saint Gobain NorPro) | 4.30 | 99.60 |
| MgO (Engelhard) | 2.60 | 99.64 |
| $MgO/V_2O_5$ | 4.20 | not determined |

Example 2

A gaseous stream of 8 g/h of aniline (doped with 500 ppm of phenol), 3.2 g/h of water and 5.76 l/h of hydrogen was passed, at ambient pressure and at 240° C., through the adsorber tube mentioned in Example 1 filled with glass beads and a packing of 10 g of adsorbent. The gas stream leaving the adsorber was condensed at 3° C. in a collecting vessel, and the phenol content was determined by gas chromatography. Table 2 compiles the phenol contents found.

TABLE 2

| | Phenol content in ppm | |
|---|---|---|
| Time t in min. | Hydrotalcite Kyowaad 500 (Kyowa Chemical) | MgO (Engelhard) |
| 30 | 7.5 | 0.0 |
| 60 | 7.4 | 0.0 |
| 90 | 7.2 | 10.9 |

TABLE 2-continued

| | Phenol content in ppm | |
|---|---|---|
| Time t in min. | Hydrotalcite Kyowaad 500 (Kyowa Chemical) | MgO (Engelhard) |
| 120 | 8.2 | 10.8 |
| 150 | 7.7 | 10.5 |
| 180 | 7.2 | 10.6 |
| 210 | 7.2 | 0.0 |
| 240 | 6.8 | 10.6 |
| 270 | 7.3 | 17.9 |
| 300 | 7.5 | 10.5 |

Example 3

A loaded adsorbent from Example 1 was regenerated by burning off all the adsorbed organic compounds, at 340° C. and at ambient pressure, in a stream of air in nitrogen. The adsorbents from Example 1 can each be regenerated and loaded again 5 times without any significant loss of activity.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for removing compounds containing phenolic hydroxy groups from a gas stream containing at least one aromatic amine generated in the course of gas-phase hydrogenation of a nitroaromatic compound with hydrogen comprising adsorbing the compounds containing phenolic hydroxy groups on a basic solid.

2. The process of claim 1 in which the gas stream passed over the basic solid has an inlet temperature of from 150 to 500° C. and an absolute pressure of from 1 to 50 bar.

3. The process of claim 1 in which the basic solid contains an oxide and/or hydroxide of an element from any of Groups 1, 2, 12, 13 or 14 of the Periodic Table of Elements.

4. The process of claim 1 in which the basic solid contains a zeolite.

5. The process of claim 1 in which the basic solid contains from 0.1 to 10 wt. % of an oxidation catalyst, based on the total weight of the basic solid (including oxidation catalyst).

6. The process of claim 5 in which the oxidation catalyst contains a metal or an oxide of a metal selected from any of Groups 5, 6, 7, 10 or 11 of the Periodic Table of Elements.

7. The process of claim 1 in which the basic solid is regenerated by treatment with an oxygen or oxygen-containing gas mixture at a temperature of from 250 to 500° C. when the basic solid is fully or partially loaded with the compounds containing phenolic hydroxy groups.

8. The process of claim 1 in which the adsorption is carried out either in a fixed bed or two or more fixed beds connected in parallel.

9. The process of claim 1 in which the gas-phase hydrogenation of the nitroaromatic compound is carried out in the presence of a stationary, heterogeneous supported catalyst, and the basic solid is the same material as the support or is applied to the support which is used as the support for the heterogeneous supported catalyst in the gas-phase hydrogenation of the nitroaromatic compound.

* * * * *